US00PP13927P29

(12) United States Plant Patent
Bergman

(10) Patent No.: US PP13,927 P2
(45) Date of Patent: Jul. 1, 2003

(54) CHRYSANTHEMUM PLANT NAMED 'RED YODULUTH'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,272

(22) Filed: Mar. 8, 2002

(51) Int. Cl.[7] ..... A01H 5/00
(52) U.S. Cl. ..... Plt./286

(58) Field of Search ..... Plt./286, 298

*Primary Examiner*—Bruce R. Campell
*Assistant Examiner*—June Hwu
(74) *Attorney, Agent, or Firm*—C. A. Whealy

(57) ABSTRACT

A distinct cultivar of Chrysanthemum plant named 'Red Yoduluth', characterized by its uniform, tall and upright plant habit; strong and freely branching growth habit; dark green foliage; uniform and freely flowering habit; daisy-type inflorescences; spoon-shaped ray florets with red-colored throats and light yellow-colored tubes; and excellent post-production longevity with plants maintaining good substance and color for about four weeks in an interior environment.

1 Drawing Sheet

BOTANICAL CLASSIFICATION/CULTIVAR DESIGNATION

*Chrysanthemum×morifolium* cultivar Red Yoduluth.

BACKGROUND OF THE INVENTION

The present Invention relates to a new and distinct cultivar of Chrysanthemum plant, botanically known as *Chrysanthemum×morifolium* and hereinafter referred to by the name 'Red Yoduluth'.

The new Chrysanthemum is a product of a mutation induction program conducted by the Inventor in Fort Myers, Fla. The objective of the program is to create new potted Chrysanthemum cultivars that are suitable for year-round production with uniform plant growth habit, good vigor, desirable inflorescence form and floret colors, fast response time, and good postproduction longevity.

The new Chrysanthemum originated by exposing unrooted cuttings of the Chrysanthemum cultivar Yoduluth, disclosed in U.S. Plant Pat. No. 11,993, to X-ray radiation in August, 1998 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered. The new Chrysanthemum was discovered and selected by the Inventor as a single flowering plant within this population in January, 1999, in a controlled environment in Fort Myers, Fla. The selection of this plant was based on its uniform plant growth habit, good vigor, desirable inflorescence form and floret colors, and excellent postproduction longevity.

Asexual reproduction of the new Chrysanthemum by vegetative tip cuttings was first conducted in Fort Myers, Fla. in April, 1999. Asexual reproduction by cuttings has shown that the unique features of this new Chrysanthemum are stable and reproduced true to type in successive generations.

SUMMARY OF THE INVENTION

The cultivar Red Yoduluth has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Red Yoduluth'. These characteristics in combination distinguish 'Red Yoduluth' as a new and distinct Chrysanthemum:

1. Uniform, tall and upright plant habit.
2. Strong and freely branching growth habit.
3. Dark green foliage.
4. Uniform and freely flowering habit.
5. Nine-week flowering response time.
6. Daisy-type inflorescences.
7. Spoon-shaped ray florets with red-colored throats and light yellow-colored tubes.
8. Excellent postproduction longevity with plants maintaining good substance and color for about four weeks in an interior environment.

Plants of the new Chrysanthemum differ primarily from plants of the cultivar Yoduluth in ray floret coloration as plants of the new Chrysanthemum have ray florets with red-colored throats whereas plants of the cultivar Yoduluth have ray florets with purple-colored throats. In addition, plants of the new Chrysanthemum have longer postproduction longevity than plants of the cultivar Yoduluth.

Plants of the new Chrysanthemum can be compared to plants of the cultivar Rage, disclosed in U.S. Plant Pat. No. 8,770. In side-by-side comparisons conducted by the Inventor in Salinas, Calif., plants of the new Chrysanthemum differed from plants of the cultivar Rage in the following characteristics:

1. Plants of the new Chrysanthemum were more vigorous than plants of the cultivar Rage.
2. Plants of the new Chrysanthemum flowered about one week later than plants of the cultivar Rage.

3. Ray florets of plants of the new Chrysanthemum were spoon-shaped with long corolla tubes whereas ray florets of plants of the cultivar Rage were mostly flat with short corolla tubes.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a side perspective view of a typical flowering plant of 'Red Yoduluth' grown as a spray-type.

The photograph at the bottom of the sheet comprises a close-up view of typical inflorescences of 'Red Yoduluth' grown as a spray-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 footcandles. Four unrooted cuttings were directly stuck in 15-cm containers, exposed to long day/short night conditions, and pinched once about 14 days later. At the time of the pinch, the photoinductive short day/long night treatments were initiated. Plants used for the photographs and description were grown as spray-types. Measurements and numerical values represent averages of typical flowering plants.

Botanical classification: *Chrysanthemum×morifolium* cultivar Red Yoduluth.

Commercial classification: Daisy-type potted Chrysanthemum.

Parentage: Induced mutation of *Chrysanthemum×morifolium* cultivar Yoduluth, disclosed in U.S. Plant Pat. No. 11,993.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous daisy-type potted Chrysanthemum that is typically grown as a spray-type. Stems mostly upright and somewhat outwardly spreading; uniform crown. Freely branching, about three to four lateral branches develop after removal of terminal apex (pinching); dense and full plants.

*Plant height.*—Tall, about 36 cm.

*Plant width.*—About 42 cm.

*Lateral branches.*—Length: About 30 cm. Diameter: About 7 mm. Internode length: About 1.6 cm. Strength: Strong. Texture: Pubescent. Color: 146A.

*Foliage description.*—Arrangement: Alternate. Length: About 8.4 cm. Width: About 5.7 cm. Apex: Cuspidate. Base: Attenuate. Margin: Palmately lobed, sinuses between lateral lobes mostly parallel. Texture: Upper surface: Sparsely pubescent. Lower surface: Pubescent; veins prominent. Color: Young foliage, upper surface: Darker than 147A. Young foliage, lower surface: Darker than 147B. Fully expanded foliage, upper surface: 147A. Fully expanded foliage, lower surface: 147B. Venation, upper surface: Close to 147A to 147B. Venation, lower surface: Close to 146A. Petiole length: About 2.5 cm. Petiole diameter: About 3 mm. Petiole color, both surfaces: Close to 146A to 146B.

Inflorescence description:

*Appearance.*—Daisy-type inflorescence form with elongated spoon-shaped ray florets. Inflorescences borne on terminals above foliage. Disk and ray florets arranged acropetally on a capitulum. Not fragrant. Typically grown as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to two weeks of long day/short night conditions followed by photoinductive short day/long night conditions flower about nine weeks later.

*Postproduction longevity.*—Inflorescences maintain good color and substance for at about four weeks in an interior environment.

*Quantity of inflorescences.*—Freely flowering, about 8 or 9 inflorescences per lateral branch.

*Inflorescence bud.*—Height: About 7 mm. Diameter: About 9 mm. Shape: Oblate. Color: Between 146A and 147A.

*Inflorescence size.*—Diameter: About 7.7 cm. Depth (height): About 1.25 cm. Diameter of disc: About 2 cm. Receptacle diameter: About 6 mm.

*Ray florets.*—Shape: Spoon-shaped. Orientation: Initially upright, then perpendicular to the peduncle. Aspect: Initially slightly incurved, then mostly flat. Length: About 3.5 cm. Width: Open spoon: About 8 mm. Tube: About 3.5 mm. Apex: Emarginate. Base: Fused into a corolla tube. Corolla tube length: Variable, about 2.2 cm. Margin: Entire. Texture: Smooth, glabrous, satiny. Number of ray florets per inflorescence: About 34 arranged in a single row. Color: When opening and fully expanded, throat: Closest to 46A. When opening and fully expanded, tube: Upper surface: 9A faintly underlain with 46A. Lower surface: 9A underlain with 46A.

*Disc florets.*—Arrangement: Massed at center of receptacle. Shape: Tubular, elongated. Apex: Five-pointed. Length: About 5.5 mm. Width: Apex: About 2 mm. Base: About 1 mm. Number of disc florets per inflorescence: About 187. Color: Immature: Close to 154A. Mature: Apex: Close to 9A. Mid-section and base: Close to 145A.

*Phyllaries.*—Quantity per inflorescence: About 24. Length: About 7.5 mm. Width: About 2 mm. Shape: Ligulate. Apex: Acute. Base: Truncate. Texture: Upper surface: Waxy, smooth. Lower surface:

Pubescent. Color: Upper surface: Close to 146A. Lower surface: Close to 147A.

*Peduncles.*—Length: First peduncle: About 5 cm. Fourth peduncle: About 9.5 cm. Seventh peduncle: About 8.75 cm. Diameter: About 2.5 mm. Angle to vertical: About 45 to 50° from vertical. Strength: Strong, flexible. Texture: Pubescent. Color: 146A.

*Reproductive organs.*—Androecium: Present on disc florets only. Anther color: Close to 12A. Pollen amount: Moderate. Pollen color: Close to 13A. Gynoecium: Present on both ray and disc florets. Style color: Close to 154A. Stigma color: Close to 9A to 12A.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Red Yoduluth', as illustrated and described.

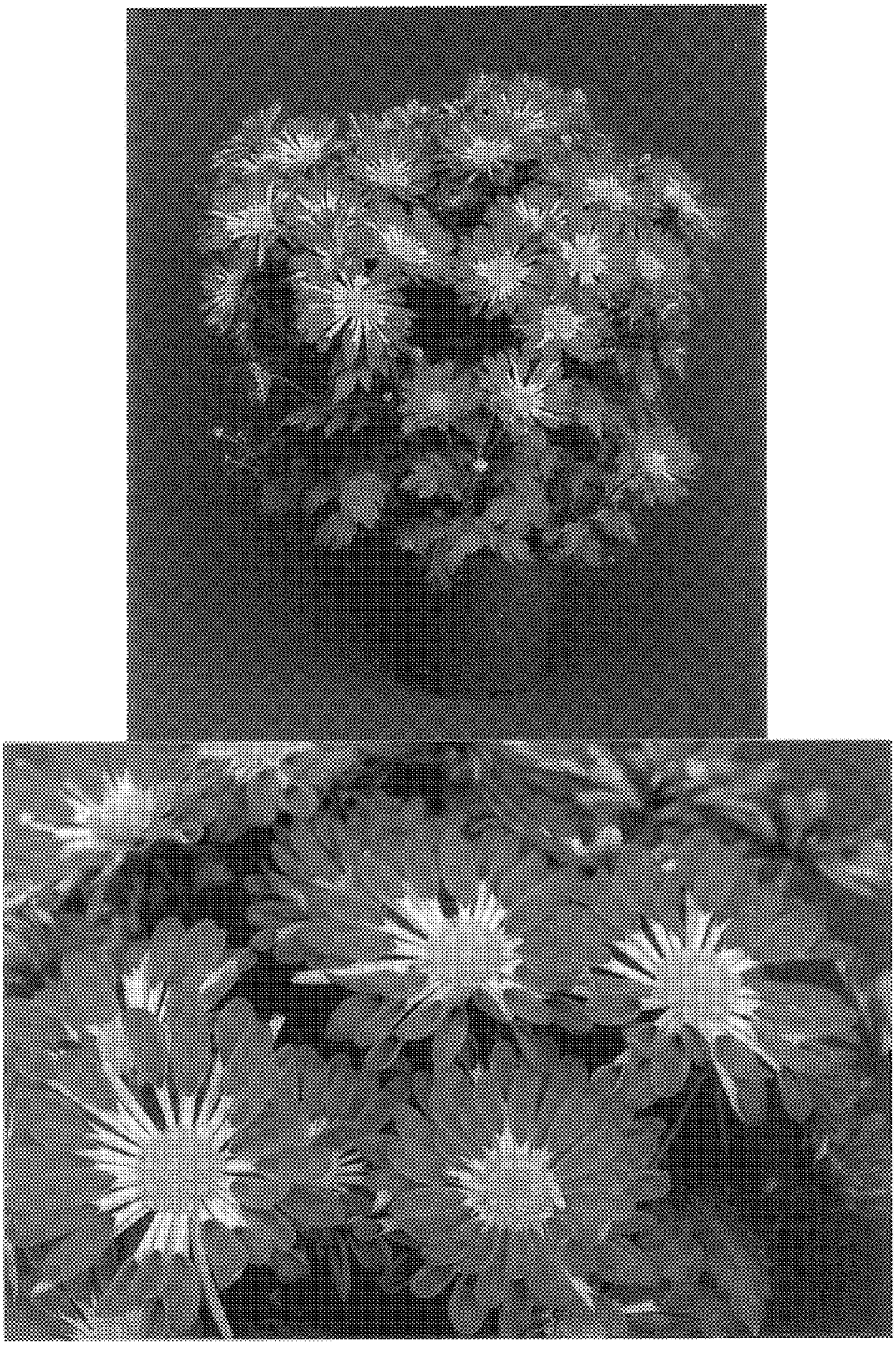

* * * * *